United States Patent

Wingert et al.

Patent Number: 5,147,892
Date of Patent: Sep. 15, 1992

[54] BENZYL KETONES AND FUNGICIDES CONTAINING THEM

[75] Inventors: Horst Wingert; Hubert Sauter, both of Mannheim; Franz Roehl, Ludwigshafen; Reinhard Doetzer, Weinheim; Gisela Lorenz, Neustadt; Eberhard Ammermann, Ludswigshafen, all of Fed. Rep. of Germany

[73] Assignee: BASF Aktiengesellschaft, Ludwigshafen, Fed. Rep. of Germany

[21] Appl. No.: 722,504

[22] Filed: Jun. 27, 1991

[30] Foreign Application Priority Data

Jun. 27, 1990 [DE] Fed. Rep. of Germany ....... 4020397

[51] Int. Cl.$^5$ .................... A01N 37/34; A61K 31/257
[52] U.S. Cl. .................... 514/522; 514/513; 514/568; 514/539; 560/19; 560/21; 560/35; 558/405; 558/406; 558/408; 558/410; 558/411; 558/414; 558/415; 562/440; 562/444; 562/452; 562/459; 562/469; 562/463; 562/473
[58] Field of Search ............... 560/35, 21, 19; 514/522, 513, 539, 568; 558/405, 408, 414, 406, 410, 411, 415; 562/440, 444, 452, 459, 463, 469, 473

[56] References Cited

FOREIGN PATENT DOCUMENTS 0253213 1/1988 European Pat. Off. .
0354571 3/1990 European Pat. Off. .

OTHER PUBLICATIONS

P. Knochel, J. Org. Chem. 53 (1988) 2390.
T. Fujisawa et al., Chem. Lett. (1981) 1135.

Primary Examiner—Jose G. Dees
Assistant Examiner—Joseph M. Conrad
Attorney, Agent, or Firm—Oblon, Spivak, McClelland, Maier & Neustadt

[57] ABSTRACT

Benzyl ketones of the formula

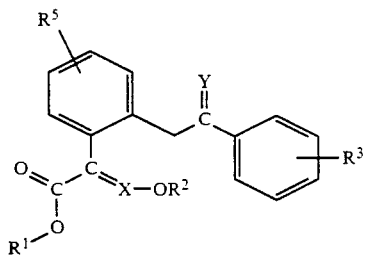

where
X is CH or N,
Y is O or NR$^4$,
R$^1$, R$^2$ are H or alkyl,
R$^3$ is halogen, cyano, nitro, alkyl, cycloalkyl, alkoxy, haloalkyl, arylalkyl, arylalkoxy, aryloxy or aryl, and the aryl groups in turn may be substituted,
R$^4$ is OH, alkoxy or arylalkoxy and
R$^5$ is H, methyl, halogen or methoxy,
and fungicides containing these compounds.

6 Claims, No Drawings

BENZYL KETONES AND FUNGICIDES CONTAINING THEM

The present invention relates to benzyl ketones, fungicides which contain these compounds and methods for controlling fungi with these compounds.

It is known that 2-(phenoxymethyl)-phenylglyoxylic acid methyl ester O-methyloxime can be used as a fungicide (European Patent 253,213). However, the fungicidal action of the compound is unsatisfactory.

It is an object of the present invention to provide active ingredients and fungicides having a better action.

We have found that this object is achieved and that benzyl ketones of the general formula I

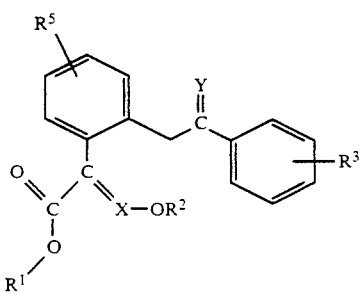

where X is CH or N, Y is O or NR$^4$, R$^1$ and R$^2$ are each H or C$_1$–C$_4$-alkyl, R$^3$ is H, halogen, cyano, nitro, C$_1$–C$_6$-alkyl, C$_3$–C$_6$-cycloalkyl, C$_1$–C$_6$-alkoxy, halo-C$_1$- or -C$_2$-alkyl, aryl-C$_1$- or -C$_2$-alkyl, aryl-C$_1$ or -C$_2$-alkoxy, aryloxy or aryl, and the aryl groups in turn may be substituted by from one to three of the radicals halogen, cyano, nitro, C$_1$–C$_6$-alkyl, C$_1$–C$_6$-alkoxy or halo-C$_1$- or -C$_2$-alkyl, R$^4$ is OH, C$_1$–C$_6$-alkoxy or aryl-C$_1$- or -C$_2$-alkoxy and R$^5$ is H, methyl, halogen or methoxy, have a better fungicidal action than the known active ingredients.

Preferred benzyl ketones of the general structural formula I

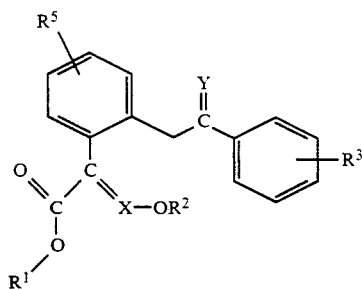

are those in which X is CH or N, Y is O or NR$^4$, R$^1$ and R$^2$ are each H or C$_1$–C$_4$-alkyl (e.g. methyl, ethyl, n- or isopropyl or n-, iso-, sec- or tert-butyl), R$^3$ is H, halogen (e.g. F, Cl, Br or I), nitro, cyano, C$_1$–C$_6$-alkyl (e.g. methyl, ethyl, n- or isopropyl, n-, iso-, sec- or tert-butyl, n-pentyl or n-hexyl), C$_3$–C$_6$-cycloalkyl (e.g. cyclopropyl, cyclobutyl, cyclopentyl or cyclohexyl), C$_1$–C$_6$-alkoxy (e.g. methoxy, ethoxy, n- or isopropoxy, n-, iso-, sec- or tert-butoxy, pentyloxy or hexyloxy), halo-C$_1$-or -C$_2$-alkyl (e.g. trifluoromethyl, trichloromethyl or pentafluoroethyl), aryl-C$_1$- or -C$_2$-alkyl (e.g. benzyl or phenylethyl), aryl-C$_1$- or -C$_2$-alkoxy (e.g. benzyloxy or phenylethoxy), aryloxy (e.g. phenoxy) or aryl (e.g. phenyl), and the aryl group in turn may be substituted by from one to three of the radicals halogen, cyano, nitro, C$_1$–C$_6$-alkyl, C$_1$–C$_6$-alkoxy or halo-C$_1$- or -C$_2$-alkyl, R$^4$ is OH, C$_1$–C$_6$-alkoxy or aryl-C$_1$- or -C$_2$-alkoxy and R$^5$ is hydrogen.

Compounds of the general structural formula I where X is CH or N, Y is O, R$^1$ and R$^2$ are each methyl, R$^3$ has the abovementioned meanings and R$^5$ is hydrogen are particularly preferred.

Because of the C=X double bond, the novel compounds of the general formula I may occur both as E and as Z isomers, which can be separated in a conventional manner. Both the individual isomeric compounds and mixtures thereof form subjects of the invention and can be used as fungicides.

The novel benzyl ketones I where Y is O are obtained, for example, by converting a benzyl halide of the general formula II in a conventional manner (cf. Houben-Weyl, Vol. 13/2 a, page 553 et seq.; P. Knochel, J. Org. Chem. 53 (1988), 2390) into an organo-zinc-copper compound of the general formula III and reacting the latter with a carbonyl halide of the general formula IV (S. C. Berk, P. Knochel and M. C. P. Yeh, J. Org. Chem. 53 (1988), 5789).

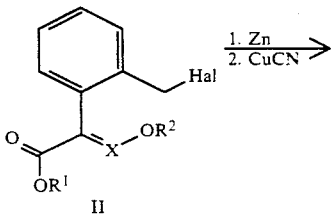

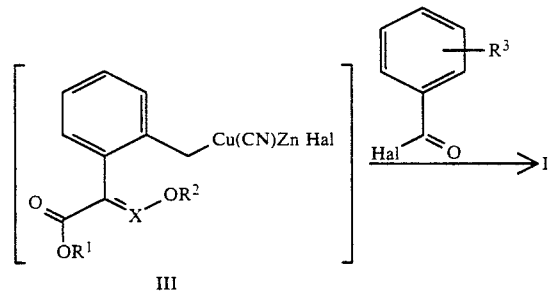

X, R$^1$, R$^2$ and R$^3$ have the same meanings as in formula I and Y is O; Hal in formulae II and III is halogen, preferably bromine; Hal in formula IV is halogen, preferably chlorine.

The benzyl halides II are reacted with activated zinc, as a rule from −5° to 10° C., preferably at 0° C. (P. Knochel, M. C. P. Yeh, S. C. Berk and J. Talbert, J. Org. Chem. 53 (1988), 2390). The reaction to give the organo-copper-zinc compound is then carried out using the tetrahydrofuran-soluble CuCN.2LiCl complex, at from −80° to −10° C.

The reaction with the carbonyl halides IV is carried out, for example, in an inert, anhydrous solvent, e.g. tetrahydrofuran, at from −70° to 30° C.

Alternatively, the compounds of the general structural formula I where Y is O can also be prepared by reacting a benzyl halide of the formula II with a carbonyl halide of the formula IV in the presence of zinc and a transition metal catalyst, e.g. Pd(Ph$_3$P)$_4$, PdCl$_2$, Pd(Ph$_3$P)$_2$Cl$_2$, Pd(PhCN)$_2$Cl$_2$, Pd(OAc)$_2$ or Ni(PPh$_3$)$_2$Cl$_2$, in an inert solvent, e.g. tetrahydrofuran, toluene or preferably dimethoxyethane, at from −10° to +100° C. (cf. T. Fujisawa et al., Chem. Lett. (1981), 1135), where Ph is phenyl.

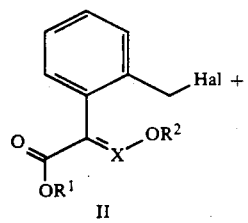

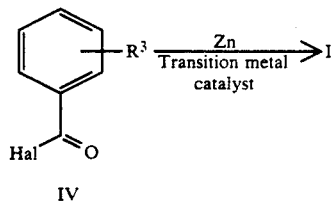

Because of the C=X double bond, the starting compounds II may be in the form of E/Z isomer mixtures or pure E or Z isomers, so that the corresponding subsequent products, including the benzyl ketones I, are obtained either as E/Z isomer mixtures or as E or Z isomers. The invention relates both to the individual isomeric compounds and to mixtures thereof.

The preparation of the starting compounds II (X=CH) is described in European Patent 226,917 and that of the compounds II (X=N) is described in European Patent 354,571.

The carbonyl halides of the general formula IV (where $R^3$ has the abovementioned meanings) are either known or can be prepared by processes similar to known processes. Appropriate preparation methods are described in, for example, Houben-Weyl, Methoden der organischen Chemie, Vol. E5, page 587.

The compounds of the general formula I where Y is $NR^4$ can be prepared from the corresponding compounds of the formula I where Y is O by reacting the latter in a conventional manner with an amine of the general structure $NH_2R^4$, where $R^4$ has the meanings stated in claim 1 (cf. Houben-Weyl, Methoden der organischen Chemie, Volume X/4, page 1).

The Examples which follow illustrate the preparation of the benzyl ketones.

EXAMPLE 1

Preparation of methyl 2-(2-chlorophenylcarbonylmethyl)-phenyl-β-methoxyacrylate (compound 5, Table 2)

700 mg of 1,2-dibromoethane are added to 2.3 g of zinc powder in 20 ml of THF (tetrahydrofuran). Refluxing is carried out until evolution of gas has ended, the mixture is allowed to cool to room temperature (20° C.) and 0.2 ml of trimethylchlorosilane is added. A solution of 10 g (35 mmol) of methyl α-(2-bromomethylphenyl)-β-methoxyacrylate in 40 ml of THF is added dropwise to this solution at 0° C. and stirring is continued for 3 hours at 5° C. Thereafter, the mixture is cooled to −78° C. and a solution of 3.2 g of copper cyanide and 3 g of lithium chloride in 40 ml of THF is added. The mixture is allowed to thaw for 5 minutes at −20° C. and is again cooled to −78° C., and a solution of 6.1 g of 2-chlorobenzoyl chloride in 20 ml of THF is added dropwise. Stirring is carried out overnight at room temperature. The reaction mixture is poured onto water and extracted with ethyl acetate, and the organic phase is dried and evaporated down. Chromatography over silica gel using hexane/ethyl acetate gives 4.1 g of compound No. 5 (Table 2) as a colorless solid of melting point 70°–75° C. Yield: 35%.

EXAMPLE 2

Methyl 2-(phenylcarbonylmethyl)-phenyl-β-methoxyacrylate (compound 1, Table 2)

A solution of 5 g (17.5 mmol) of methyl α-(2-bromomethylphenyl)-β-methoxyacrylate and 2.5 g (17.8 mmol) of benzoyl chloride in 50 ml of dimethoxyethane is added dropwise to 2.3 g (0.035 mol) of zinc powder and 600 mg (0.9 mmol) of $Pd(Ph_3P)_2Cl_2$ under nitrogen and the mixture is then heated at 50° C. for 30 minutes. Water is added, the mixture is extracted with ethyl acetate and the organic phase is dried and evaporated down. The residue is chromatographed over silica gel using hexane/ethyl acetate. 1.6 g of compound No. 1 (Table 1) are obtained as a pale yellow solid of melting point 97°–99° C. Yield: 29%.

The compounds given in the tables below may be prepared analogously.

TABLE 1

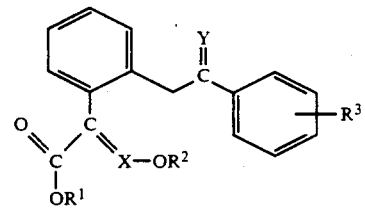

| No. | X | Y | $R^1$ | $R^2$ | $R^3$ | $R^4$ | Phys. data (mp., IR) |
|---|---|---|---|---|---|---|---|
| 1 | N | O | H | $CH_3$ | H | — | |
| 2 | N | O | $CH_3$ | H | H | — | |
| 3 | N | O | $C_2H_5$ | $CH_3$ | H | — | |
| 4 | N | O | $n-C_3H_5$ | $CH_3$ | H | — | |
| 5 | N | O | $CH_3$ | $C_2H_5$ | H | — | |
| 6 | N | O | $CH_3$ | $n-C_3H_5$ | H | — | |
| 7 | N | $NR^4$ | $CH_3$ | $CH_3$ | H | OH | |
| 8 | N | $NR^4$ | $CH_3$ | $CH_3$ | H | $OCH_3$ | |
| 9 | N | $NR^4$ | $CH_3$ | $CH_3$ | H | $OC_2H_5$ | |
| 10 | N | $NR^4$ | $CH_3$ | $CH_3$ | H | $O(n-C_3H_7)$ | |
| 11 | N | $NR^4$ | $CH_3$ | $CH_3$ | H | $OCH_2C_6H_5$ | |
| 12 | CH | O | $C_2H_5$ | $CH_3$ | H | — | |
| 13 | CH | O | $n-C_3H_7$ | $CH_3$ | H | — | |
| 14 | CH | $NR^4$ | $CH_3$ | $CH_3$ | H | $OCH_3$ | |
| 15 | CH | $NR^4$ | $CH_3$ | $CH_3$ | H | $OC_2H_5$ | |
| 16 | CH | $NR^4$ | $CH_3$ | $CH_3$ | H | $OCH_2C_6H_5$ | |

TABLE 2

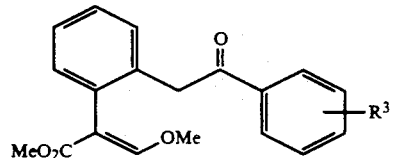

| No. | $R^3$ | Phys. data (mp., IR) |
|---|---|---|
| 1 | H | 97–99° C. |
| 2 | 2-F | |
| 3 | 3-F | |
| 4 | 4-F | |

TABLE 2-continued

[Structure: 2-substituted phenyl group with CH2-C(=O)-phenyl-R³ and =CH-OMe, MeO2C substituents]

| No. | R³ | Phys. data (mp., IR) |
|---|---|---|
| 5 | 2-Cl | 70–75° C. |
| 6 | 3-Cl | 93–108° C. |
| 7 | 4-Cl | 111–117° C. |
| 8 | 2-Br | |
| 9 | 3-Br | |
| 10 | 4-Br | |
| 11 | 2-I | |
| 12 | 3-I | |
| 13 | 4-I | |
| 14 | 2-CN | |
| 15 | 3-CN | |
| 16 | 4-CN | |
| 17 | 2-NO$_2$ | |
| 18 | 3-NO$_2$ | |
| 19 | 4-NO$_2$ | |
| 20 | 2-Methyl | 76–82° C. |
| 21 | 3-Methyl | 67–71° C. |
| 22 | 4-Methyl | 88–91° C. |
| 23 | 2-Ethyl | |
| 24 | 3-Ethyl | |
| 25 | 4-Ethyl | |
| 26 | 2-n-Propyl | |
| 27 | 3-n-Propyl | |
| 28 | 4-n-Propyl | |
| 29 | 2-iso-Propyl | |
| 30 | 3-iso-Propyl | |
| 31 | 4-iso-Propyl | |
| 32 | 2-n-Butyl | |
| 33 | 3-n-Butyl | |
| 34 | 4-n-Butyl | |
| 35 | 2-iso-Butyl | |
| 36 | 3-iso-Butyl | |
| 37 | 4-iso-Butyl | |
| 38 | 2-sec-Butyl | |
| 39 | 3-sec-Butyl | |
| 40 | 4-sec-Butyl | |
| 41 | 2-tert.-Butyl | |
| 42 | 3-tert.-Butyl | |
| 43 | 4-tert.-Butyl | |
| 44 | 2-n-Pentyl | |
| 45 | 3-n-Pentyl | |
| 46 | 4-n-Pentyl | |
| 47 | 2-n-Hexyl | |
| 48 | 3-n-Hexyl | |
| 49 | 4-n-Hexyl | |
| 50 | 2-Cyclopropyl | |
| 51 | 3-Cyclopropyl | |
| 52 | 4-Cyclopropyl | |
| 53 | 2-Cyclohexyl | |
| 54 | 3-Cyclohexyl | |
| 55 | 4-Cyclohexyl | |
| 56 | 2-Methoxy | |
| 57 | 3-Methoxy | |
| 58 | 4-Methoxy | |
| 59 | 2-Ethoxy | |
| 60 | 3-Ethoxy | |
| 61 | 4-Ethoxy | |
| 62 | 2-n-Propoxy | |
| 63 | 3-n-Propoxy | |
| 64 | 4-n-Propoxy | |
| 65 | 2-iso-Propoxy | |
| 66 | 3-iso-Propoxy | |
| 67 | 4-iso-Propoxy | |
| 68 | 2-tert.-Butoxy | |
| 69 | 3-tert.-Butoxy | |
| 70 | 4-tert.-Butoxy | |
| 71 | 2-CF$_3$ | |
| 72 | 3-CF$_3$ | |
| 73 | 4-CF$_3$ | |
| 74 | 2-Benzyl | |
| 75 | 3-Benzyl | |
| 76 | 4-Benzyl | |
| 77 | 2-[4-Chlorobenzyl] | |
| 78 | 2-[4-Methoxy-benzyl] | |
| 79 | 4-Methoxy-3-benzyl | |
| 80 | 2-[2-Phenylethyl] | |
| 81 | 3-[2-Phenylethyl] | |
| 82 | 4-[2-Phenylethyl] | |
| 83 | 2-Benzyloxy | |
| 84 | 3-Benzyloxy | |
| 85 | 4-Benzyloxy | |
| 86 | 2-Phenoxy | |
| 87 | 3-Phenoxy | 1706, 1683, 1631, 1580, 1489 1435, 1250, 1128 (cm$^{-1}$) |
| 88 | 4-Phenoxy | |
| 89 | 2-Phenyl | |
| 90 | 3-Phenyl | |
| 91 | 4-Phenyl | |
| 92 | 2-[3-Br, 4-Me-phenyl] | |
| 93 | 2-[4-Me-phenyl] | |
| 94 | 4-[4-Et-phenyl] | |
| 95 | 4-[4-n-Propyl-phenyl] | |
| 96 | 4-[4-Bromophenoxy] | |
| 97 | 2,3-F$_2$ | |
| 98 | 2,4-F$_2$ | |
| 99 | 2,5-F$_2$ | |
| 100 | 2,6-F$_2$ | |
| 101 | 3,4-F$_2$ | |
| 102 | 3,5-F$_2$ | |
| 103 | 2,3-Cl$_2$ | |
| 104 | 2,4-Cl$_2$ | |
| 105 | 2,5-Cl$_2$ | |
| 106 | 2,6-Cl$_2$ | |
| 107 | 3,4-Cl$_2$ | |
| 108 | 3,5-Cl$_2$ | |
| 109 | 2,5-Br$_2$ | |
| 110 | 2-Cl, 4-Br | |
| 111 | 2-Cl, 5-Br | |
| 112 | 2-F, 6-Cl | |
| 113 | 3-Cl, 6-Br | |
| 114 | 4-F, 5-Br | |
| 115 | 2-F, 4-Cl | |
| 116 | 4-F, 5-Cl | |
| 117 | 2-F, 3-Cl | |
| 118 | 4-F, 2-Cl | |
| 119 | 2-Cl, 6-Me | |
| 120 | 3-Cl, 2-Me | |
| 121 | 3-Cl, 4-Me | |
| 122 | 3-Cl, 6-Me | |
| 123 | 4-Cl, 5-Me | |
| 124 | 4-Cl, 6-Me | |
| 125 | 3-F, 4-Me | |
| 126 | 3-F, 6-Me | |
| 127 | 2-Cl, 5-Me | |
| 128 | 2,6-Cl$_2$, 3-Me | |
| 129 | 3-CN, 4-Me | |
| 130 | 2,3-Me$_2$ | 92–97° C. |
| 131 | 2,4-Me$_2$ | |
| 132 | 2,5-Me$_2$ | |
| 133 | 2,6-Me$_2$ | |
| 134 | 3,4-Me$_2$ | |
| 135 | 3,5-Me$_2$ | |
| 136 | 2,4,6-Me$_3$ | |
| 137 | 2,6-(CF$_3$)$_2$ | |
| 138 | 2,4-(CF$_3$)$_2$ | |
| 139 | 3,5-(CF$_3$)$_2$ | |
| 140 | 2-F, 4-CF$_3$ | |
| 141 | 3-F, 5-CF$_3$ | |
| 142 | 4-F, 3-CF$_3$ | |
| 143 | 2-Cl, 4-CF$_3$ | |
| 144 | 2,3-(OCH$_3$)$_2$ | |
| 145 | 2,4-(OCH$_3$)$_2$ | |
| 146 | 2,5-(OCH$_3$)$_2$ | |
| 147 | 2,6-(OCH$_3$)$_2$ | |

TABLE 2-continued

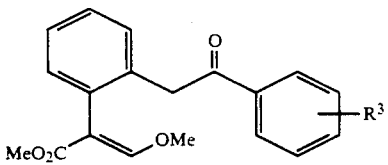

| No. | R³ | Phys. data (mp., IR) |
|---|---|---|
| 148 | 3,4-(OCH₃)₂ | |
| 149 | 3,5-(OCH₃)₂ | |
| 150 | 2-OCH₃, 3-CH₃ | |
| 151 | 2-OCH₃, 4-CH₃ | |
| 152 | 2-OCH₃, 5-CH₃ | |
| 153 | 2-OCH₃, 4-Cl | |
| 154 | 2-OCH₃, 5-Cl | |
| 155 | 2-OCH₃, 3,5-Cl₂ | |
| 156 | 2-OCH₃, 3,6-Cl₂ | |
| 157 | 2,6-(OCH₃)₂, 3-Cl | |
| 158 | 4-OCH₃, 2-Cl | |
| 159 | 4-OCH₃, 3-Cl | |
| 160 | 4-OCH₃, 3-F | |
| 161 | 4-OCH₃, 2-CH₃ | |

Me = Methyl

TABLE 3

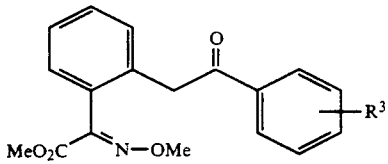

| No. | R³ | Phys. data (mp., IR) |
|---|---|---|
| 1 | H | |
| 2 | 2-F | |
| 3 | 3-F | |
| 4 | 4-F | |
| 5 | 2-Cl | |
| 6 | 3-Cl | |
| 7 | 4-Cl | |
| 8 | 2-Br | |
| 9 | 3-Br | |
| 10 | 4-Br | |
| 11 | 2-I | |
| 12 | 3-I | |
| 13 | 4-I | |
| 14 | 2-CN | |
| 15 | 3-CN | |
| 16 | 4-CN | |
| 17 | 2-NO₂ | |
| 18 | 3-NO₂ | |
| 19 | 4-NO₂ | |
| 20 | 2-Methyl | 80–84° C. |
| 21 | 3-Methyl | 89–92° C. |
| 22 | 4-Methyl | |
| 23 | 2-Ethyl | |
| 24 | 3-Ethyl | |
| 25 | 4-Ethyl | |
| 26 | 2-n-Propyl | |
| 27 | 3-n-Propyl | |
| 28 | 4-n-Propyl | |
| 29 | 2-iso-Propyl | |
| 30 | 3-iso-Propyl | |
| 31 | 4-iso-Propyl | |
| 32 | 2-n-Butyl | |
| 33 | 3-n-Butyl | |
| 34 | 4-n-Butyl | |
| 35 | 2-iso-Butyl | |
| 36 | 3-iso-Butyl | |
| 37 | 4-iso-Butyl | |
| 38 | 2-sec-Butyl | |
| 39 | 3-sec-Butyl | |
| 40 | 4-sec-Butyl | |
| 41 | 2-tert.-Butyl | |

TABLE 3-continued

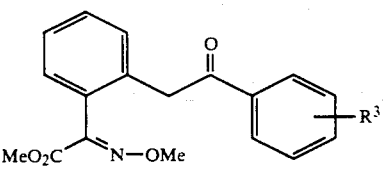

| No. | R³ | Phys. data (mp., IR) |
|---|---|---|
| 42 | 3-tert.-Butyl | |
| 43 | 4-tert.-Butyl | |
| 44 | 2-n-Pentyl | |
| 45 | 3-n-Pentyl | |
| 46 | 4-n-Pentyl | |
| 47 | 2-n-Hexyl | |
| 48 | 3-n-Hexyl | |
| 49 | 4-n-Hexyl | |
| 50 | 2-Cyclopropyl | |
| 51 | 3-Cyclopropyl | |
| 52 | 4-Cyclopropyl | |
| 53 | 2-Cyclohexyl | |
| 54 | 3-Cyclohexyl | |
| 55 | 4-Cyclohexyl | |
| 56 | 2-Methoxy | |
| 57 | 3-Methoxy | |
| 58 | 4-Methoxy | |
| 59 | 2-Ethoxy | |
| 60 | 3-Ethoxy | |
| 61 | 4-Ethoxy | |
| 62 | 2-n-Propoxy | |
| 63 | 3-n-Propoxy | |
| 64 | 4-n-Propoxy | |
| 65 | 2-iso-Propoxy | |
| 66 | 3-iso-Propoxy | |
| 67 | 4-iso-Propoxy | |
| 68 | 2-tert.-Butoxy | |
| 69 | 3-tert.-Butoxy | |
| 70 | 4-tert.-Butoxy | |
| 71 | 2-CF₃ | |
| 72 | 3-CF₃ | |
| 73 | 4-CF₃ | |
| 74 | 2-Benzyl | |
| 75 | 3-Benzyl | |
| 76 | 4-Benzyl | |
| 77 | 2-[4-Chlorobenzyl] | |
| 78 | 2-[4-Methoxy-benzyl] | |
| 79 | 4-Methoxy-3-benzyl | |
| 80 | 2-[2-Phenylethyl] | |
| 81 | 3-[2-Phenylethyl] | |
| 82 | 4-[2-Phenylethyl] | |
| 83 | 2-Benzyloxy | |
| 84 | 3-Benzyloxy | |
| 85 | 4-Benzyloxy | |
| 86 | 2-Phenoxy | |
| 87 | 3-Phenoxy | |
| 88 | 4-Phenoxy | |
| 89 | 2-Phenyl | |
| 90 | 3-Phenyl | |
| 91 | 4-Phenyl | |
| 92 | 2-[3-Br, 4-Me-phenyl] | |
| 93 | 2-[4-Me-phenyl] | |
| 94 | 4-[4-Et-phenyl] | |
| 95 | 4-[4-n-propyl-phenyl] | |
| 96 | 4-[4-Bromophenoxy] | |
| 97 | 2,3-F₂ | |
| 98 | 2,4-F₂ | |
| 99 | 2,5-F₂ | |
| 100 | 2,6-F₂ | |
| 101 | 3,4-F₂ | |
| 102 | 3,5-F₂ | |
| 103 | 2,3-Cl₂ | |
| 104 | 2,4-Cl₂ | |
| 105 | 2,5-Cl₂ | |
| 106 | 2,6-Cl₂ | |
| 107 | 3,4-Cl₂ | |
| 108 | 3,5-Cl₂ | |
| 109 | 2,5-Br₂ | |
| 110 | 2-Cl, 4-Br | |
| 111 | 2-Cl, 5-Br | |
| 112 | 2-F, 6-Cl | |

TABLE 3-continued

Structure: phenyl ring with ortho-CH2-C(=O)-phenyl-R³ substituent and ortho-C(=N-OMe)(CO2Me) group

| No. | R³ | Phys. data (mp., IR) |
|---|---|---|
| 113 | 3-Cl, 6-Br | |
| 114 | 4-F, 5-Br | |
| 115 | 2-F, 4-Cl | |
| 116 | 4-F, 5-Cl | |
| 117 | 2-F, 3-Cl | |
| 118 | 4-F, 2-Cl | |
| 119 | 2-Cl, 6-Me | |
| 120 | 3-Cl, 2-Me | |
| 121 | 3-Cl, 4-Me | |
| 122 | 3-Cl, 6-Me | |
| 123 | 4-Cl, 5-Me | |
| 124 | 4-Cl, 6-Me | |
| 125 | 3-F, 4-Me | |
| 126 | 3-F, 6-Me | |
| 127 | 2-Cl, 5-Me | |
| 128 | 2,6-Cl$_2$, 3-Me | |
| 129 | 3-CN, 4-Me | |
| 130 | 2,3-Me$_2$ | |
| 131 | 2,4-Me$_2$ | |
| 132 | 2,5-Me$_2$ | |
| 133 | 2,6-Me$_2$ | |
| 134 | 3,4-Me$_2$ | |
| 135 | 3,5-Me$_2$ | |
| 136 | 2,4,6-Me$_3$ | |
| 137 | 2,6-(CF$_3$)$_2$ | |
| 138 | 2,4-(CF$_3$)$_2$ | |
| 139 | 3,5-(CF$_3$)$_2$ | |
| 140 | 2-F, 4-CF$_3$ | |
| 141 | 3-F, 5-CF$_3$ | |
| 142 | 4-F, 3-CF$_3$ | |
| 143 | 2-Cl, 4-CF$_3$ | |
| 144 | 2,3-(OCH$_3$)$_2$ | |
| 145 | 2,4-(OCH$_3$)$_2$ | |
| 146 | 2,5-(OCH$_3$)$_2$ | |
| 147 | 2,6-(OCH$_3$)$_2$ | |
| 148 | 3,4-(OCH$_3$)$_2$ | |
| 149 | 3,5-(OCH$_3$)$_2$ | |
| 150 | 2-OCH$_3$, 3-CH$_3$ | |
| 151 | 2-OCH$_3$, 4-CH$_3$ | |
| 152 | 2-OCH$_3$, 5-CH$_3$ | |
| 153 | 2-OCH$_3$, 4-Cl | |
| 154 | 2-OCH$_3$, 5-Cl | |
| 155 | 2-OCH$_3$, 3,5-Cl$_2$ | |
| 156 | 2-OCH$_3$, 3,6-Cl$_2$ | |
| 157 | 2,6-(OCH$_3$)$_2$, 3-Cl | |
| 158 | 4-OCH$_3$, 2-Cl | |
| 159 | 4-OCH$_3$, 3-Cl | |
| 160 | 4-OCH$_3$, 3-F | |
| 161 | 4-OCH$_3$, 2-CH$_3$ | |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,
*Erysiphe cichoracearum* and Sphaerotheca fuliginea in cucurbits,
*Podosphaera leucotricha* in apples,
*Uncinula necator* in vines,
*Puccinia* species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercespora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi. Either the fungi themselves, or the plants, seed or materials to be protected against fungal attack, or the soil are treated with a fungicidally effective amount of the active ingredient.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as ligninsulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on Paecilomyces variotii. When the compounds are used for treating seed, amounts of from 0.001 to 50, and preferably from 0.01 to 10, g per kg of seed are generally sufficient.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of compound no. 20 (Table 3) and 10 parts by weight of N-methyl-α-pyrrolidone, which is suitable for application in the form of very fine drops.

II. A mixture of 20 parts by weight of compound no. 5 (Table 2), 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 6 (Table 2), 40 parts by weight of cyclohexanone, 30 parts by weight of isobutanol, 20 parts by weight of the adduct of 40 moles of ethylene oxide and 1 mole of castor oil. By finely dispersing this solution in water, an aqueous dispersion is obtained.

IV. An aqueous dispersion of 20 parts by weight of compound no. 20 (Table 2), 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By finely distributing this solution in water, an aqueous dispersion is obtained.

V. A hammer-milled mixture of 80 parts by weight of compound no. 20 (Table 3), 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 21 (Table 3) and 97 parts by weight of particulate kaolin. The dust contains 3 wt % of the active ingredient.

VII. An intimate mixture of 30 parts by weight of compound no. 20 (Table 3), 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 21 (Table 3), 10 parts of the sodium salt of a phenolsulfonic acid-ureaformaldehyde condensate, 2 parts of silica gel and 48 parts of water, which dispersion can be further diluted.

IX. A stable oily dispersion of 20 parts by weight of compound no. 20 (Table 2), 2 parts by weight of the calcium salt of dodecylbenzenesulfonic acid, 8 parts by weight of a fatty alcohol polyglycol ether, 2 parts by weight of the sodium salt of a phenolsulfonic acid-ureaformaldehyde condensate and 68 parts by weight of a paraffinic mineral oil.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

USE EXAMPLES

The prior art active ingredient 2-(phenoxymethyl)-phenylglyoxylic acid methyl ester-O-methyloxime (A) disclosed in EP 253,213 was used for comparison purposes.

USE EXAMPLE 1

Action on *Botrytis cinerea*

Paprika seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves.

The results show that active ingredient no. 20 (Table 3), employed as a 0.05 wt % spray liquor, has a better fungicidal action (55%) than prior art comparative agent A (30%).

USE EXAMPLE 2

Action on *Pyrenophora teres*

Barley seedlings of the "Igri" variety were sprayed to runoff at the 2-leaf stage with aqueous suspensions containing (dry basis) 80% of active ingredient and 20% emulsifier. After 24 hours the plants were inoculated with a spore suspension of the fungus *Pyrenophora teres* and placed for 48 hours in a high-humidity climatic cabinet kept at 18° C. The plants were then cultivated for a further 5 days in the greenhouse at 20°-22° C. and a relative humidity of 70%. The extent of fungus spread was then determined.

The results show that active ingredients nos. 5, 6 and 20 from Table 2 and nos. 20 and 21 from Table 3, when applied as a 0.05% spray liquor, have a better fungicidal action (65%) than prior art comparative agent A (30%).

We claim:

1. A benzyl ketone of the formula I

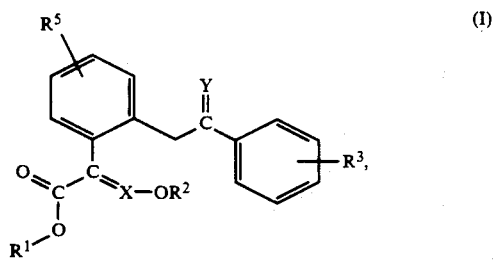

where
X is CH or N,
Y is O or NR$^4$,
R$^1$ and R$^2$ are each H or C$_1$-C$_4$-alkyl,
R$^3$ is H, halogen, cyano, nitro, C$_1$-C$_6$-alkyl, C$_3$-C$_6$-cycloalkyl, C$_1$-C$_6$-alkoxy, halo-C$_1$-C$_2$-alkyl, aryl-C$_1$-C$_2$-alkyl, aryl-C$_1$-C$_2$-alkoxy, aryloxy or aryl, and the aryl groups in turn may be substituted by from one to three of the radicals halogen, cyano, nitro, C$_1$-C$_6$-alkyl, C$_1$-C$_6$-alkoxy or halo-C$_1$-C$_2$-alkyl,
R$^4$ is OH, C$_1$-C$_6$-alkoxy or aryl-C$_1$-C$_2$-alkoxy and
R$^5$ is H, methyl, halogen or methoxy.

2. A compound of the formula I as set forth in claim 1, where R$^1$ and R$^2$ are methyl, Y is O, X is CH and R$^3$ is hydrogen.

3. A compound of the formula I as set forth in claim 1, where $R^1$ and $R^2$ are methyl, Y is O, X is N and $R^3$ is methyl in the 2-position.

4. A compound of the formula I as set forth in claim 1, where $R^1$ and $R^2$ are methyl, Y is O, X is CH and $R^3$ is methyl in the 2-position.

5. A fungicidal agent containing an inert carrier and a fungicidally effective amount of a compound of the formula I

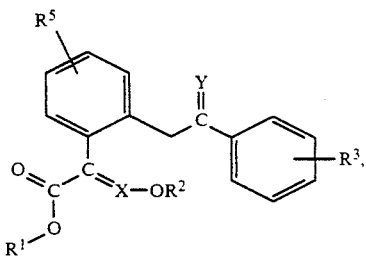
(I)

where
X is CH or N,
Y is O or $NR^4$,
$R^1$ and $R^2$ are each H or $C_1$–$C_4$-alkyl,
$R^3$ is H, halogen, cyano, nitro, $C_1$–$C_6$-alkyl, $C_3$–$C_6$-cycloalkyl, $C_1$–$C_6$-alkoxy, halo-$C_1$–$C_2$-alkyl, aryl-$C_1$–$C_2$-alkyl, aryl-$C_1$–$C_2$-alkoxy, aryloxy or aryl, and the aryl groups in turn may be substituted by from one to three of the radicals halogen, cyano, nitro, $C_1$–$C_6$-alkyl, $C_1$–$C_6$-alkoxy or halo-$C_1$–$C_2$-alkyl, $R^4$ is OH, $C_1$–$C_6$-alkoxy or aryl-$C_1$–$C_2$-alkoxy and
$R^5$ is H, methyl, halogen or methoxy.

6. A process for combating fungi, wherein the fungi or the plants, seed, materials or areas threatened by fungus attack are treated with a fungicidally effective amount of a compound of the formula I

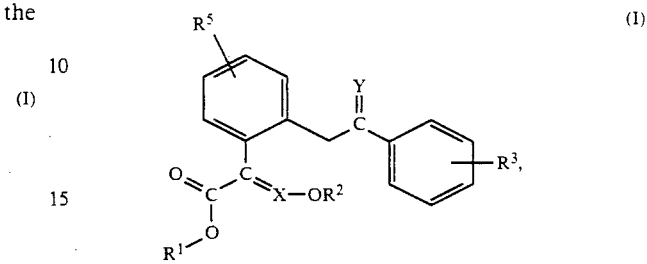
(I)

where
X is CH or N,
Y is O or $NR^4$,
$R^1$ and $R^2$ are each H or $C_1$–$C_4$-alkyl,
$R^3$ is H, halogen, cyano, nitro, $C_1$–$C_6$-alkyl, $C_3$–$C_6$-cycloalkyl, $C_1$–$C_6$-alkoxy, halo-$C_1$–$C_2$-alkyl, aryl-$C_1$–$C_2$-alkyl, aryl-$C_1$–$C_2$-alkoxy, aryloxy or aryl, and the aryl groups in turn may be substituted by from one to three of the radicals halogen, cyano, nitro, $C_1$–$C_6$-alkyl, $C_1$–$C_6$-alkoxy or halo-$C_1$–$C_2$-alkyl,
$R^4$ is OH, $C_1$–$C_6$-alkoxy or aryl-$C_1$–$C_2$-alkoxy and
$R^5$ is H, methyl, halogen or methoxy.

* * * * *